(12) United States Patent
Abudula et al.

(10) Patent No.: US 11,124,897 B1
(45) Date of Patent: Sep. 21, 2021

(54) BIODEGRADABLE CORE-SHELL FIBROUS SCAFFOLDS FOR CONTROLLED OXYGEN AND DRUG RELEASE

(71) Applicant: KING ABDULAZIZ UNIVERSITY, Jeddah (SA)

(72) Inventors: Tuerdimaimaiti Abudula, Jeddah (SA); Kalamegam Gauthaman, Jeddah (SA); Ahmed Alshahrie, Jeddah (SA); Numan Salah, Jeddah (SA); Adnan Memic, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/023,894

(22) Filed: Sep. 17, 2020

(51) Int. Cl.
| | |
|---|---|
| *A61L 15/26* | (2006.01) |
| *A61L 15/32* | (2006.01) |
| *A61L 15/44* | (2006.01) |
| *D01D 5/00* | (2006.01) |
| *D01D 5/34* | (2006.01) |
| *B82Y 5/00* | (2011.01) |

(52) U.S. Cl.
CPC .............. *D01D 5/003* (2013.01); *A61L 15/26* (2013.01); *A61L 15/32* (2013.01); *A61L 15/44* (2013.01); *D01D 5/0069* (2013.01); *D01D 5/34* (2013.01); *A61L 2300/104* (2013.01); *A61L 2300/25* (2013.01); *A61L 2300/406* (2013.01); *A61L 2300/602* (2013.01); *A61L 2300/80* (2013.01); *A61L 2400/12* (2013.01); *B82Y 5/00* (2013.01); *D10B 2211/00* (2013.01); *D10B 2331/041* (2013.01); *D10B 2509/022* (2013.01)

(58) Field of Classification Search
CPC ........... D01D 5/00; D01D 5/007; D01D 5/003
See application file for complete search history.

(56) References Cited

U.S. PATENT DOCUMENTS

| | | | | |
|---|---|---|---|---|
| 2010/0303881 | A1* | 12/2010 | Hoke ................... | A61L 31/16 424/423 |
| 2012/0193836 | A1* | 8/2012 | Sharma ................ | D01D 5/34 264/465 |
| 2012/0208421 | A1* | 8/2012 | Qi ........................ | D04H 1/728 442/334 |
| 2017/0042822 | A1* | 2/2017 | Chen .................... | A61L 31/16 |

OTHER PUBLICATIONS

Abdula et al., Materials (Basel). Mar. 2018; 11(3): 451, 12 pgs.*
Abdula et al., Materials, 2018, 11, 451, 1-12.*
Enis et al., J Industral Textiles, 2017, 47, 1, 57-70.*
Ding et al., Biosurface and Biotechnology 2, 2016, 121-136).*

* cited by examiner

*Primary Examiner* — Kyle A Purdy
(74) *Attorney, Agent, or Firm* — W & C IP

(57) ABSTRACT

Coaxial electrospinning is used to encapsulate a chitin-lignin based hybrid gel with polycaprolactone (PCL). Antibiotics and/or other bioactive agents loaded into the core and/or shell layer of the fibrous platform are released in a controlled and sustained manner that effectively inhibits both Gram-positive and Gram-negative bacteria without cytotoxicity to mammalian cells. The PCL shell layer provides longer life for the CL gels in a wet environment and allows sustainable drug release. The PCL-coated CL nanofiber scaffolds can be loaded with antimicrobial nanoparticles, antibiotics, oxygen-releasing agents, antioxidants and/or growth factors that promote healing when used as a controlled drug release dressing for chronic wounds, such as diabetic ulcers.

17 Claims, 11 Drawing Sheets

BIODEGRADABLE CORE-SHELL FIBROUS SCAFFOLDS FOR CONTROLLED OXYGEN AND DRUG RELEASE

BACKGROUND OF THE INVENTION

Field of the Invention

The invention generally relates to methods of drug encapsulation with chitin-lignin hybrid gel and polycaprolactone as a scaffold for controlled oxygen and drug delivery. The invention further relates to methods of treatment with controlled drug delivery to promote healing and inhibit or prevent side effects.

Background

Diabetic ulcers and other chronic wounds are a major healthcare burden and a source of staggering costs in both developing and developed countries. The hostile microenvironment of chronic wound is often characterized by elevated local pH levels, the excessive presence of degradative enzymes, and limited nutrient and oxygen supply. Such an environment suppresses tissue regeneration and supports the growth of pathogens leading to serious infection. Treatment of a chronic wound requires effective drug delivery systems that can stimulate physiological processes at the right time. Such drug delivery systems should take into consideration the various, concurrent physiological processes that lead to tissue regeneration. Developing biomaterials that can both serve as wound dressings and control the release of drugs could improve treatment outcomes and simultaneously minimize the negative side effects. Controlling bacterial infection is one of the most critical challenges in wound healing management. Traditionally oral and intravenous administrations of antibiotics have been commonly used for the infection treatment. However, the localized delivery of antibiotics or antimicrobial nanoparticles targets only the wound area, representing a more promising approach to fighting infection, preventing drug resistance, and lowering the risk of adverse side effects. Another major issue in the wound healing is oxygen deprivation in the wound area, because of improper or insufficient angiogenesis and vascularization. A sufficient diffusion of oxygen is critical for cell viability and growth, in order to facilitate tissue regeneration. Shortage of oxygen supply in the wound could lead to hypoxia, and consequently cell apoptosis and tissue necrosis. Formation of blood vessels and their infiltration within the scaffold throughout neoangiogenesis is essential, but often takes one-to-two weeks. The time required for neoangiogenesis could be even longer in patients suffering from diabetes. Additionally, antioxidant agents and growth factors are also key considerations for the effective treatment of chronic and acute wounds.

In recent years, electrospinning has gained much popularity for wound healing and other bioengineering application. It is a versatile technique to produce fibrous scaffolds with diameter from sub-nanometer to several micrometers, which can mimic properties of the native skin extracellular matrix (ECM). Morphology and size dimensions of the electrospun fibers can be governed by numerous parameters including polymer concentration, solution viscosity, applied voltage, feed rate, and humidity. In addition, growth factors and drugs can be encapsulated due to the higher surface area and higher porosity of the electrospun mesh. In electrospinning, the drugs can be uniformly dispersed into the nano/micro-sized fibrous polymer mesh without aggregation and quantitative loss (Ding et al. 2019, *Adv Funct Mater* 29, 1802852; Khan et al. 2018, *J Biomed Nanotech* 14:553-563). Moreover, the adaptability of the electrospinning facilitates desirable drug loading/release by providing different drug loading approaches (Hu et al. 2014, *J Controlled Release* 186:12-21; Duan et al. 2017, *Biomacromolecules* 18:3215-3221; Nguyen et al. 2015, *Int. J. Pharm.* 439:296-306; Yu et al. 2015, *ACS Applied Materials & Interfaces* 7:18891-18897).

Employing coaxial electrospinning has become a popular approach to control the drug release in the recent years (Wang et al. 2019, *Internat J Pharmaceutics* 556:363-371 (2019); Pant et al. 2019, *Pharmaceutics* 11:305). Especially combining natural gel polymers and synthetic polymers as a core-shell form can get a maximum benefit from this technology. Adeli-Sardou et al. encapsulated lawsone loaded gelatin with PCL by coaxial electrospinning, in order to decelerate biodegradation and drug release rate of gelatin. The fabricated scaffold is suggested for wound healing application, due to its suitable structural, mechanical, and biochemical characteristics, and excellent biocompatibility (Adeli-Sardou et al. 2019, *Internat J Bio Macromol* 124:478-491) Chen et al. applied coaxial electrospinning to wrap chitin derived glucosamine sulfate (GAS) into PCL, in which sustainable release of GAS could promote proliferation and growth of chondrocytes in cartilage tissue regeneration (Chen et al. 2020. *Carb Polymers* 229:115544).

Various types of gels have been electrospun for wound dressing applications including sol-gels and hydrogels that are all meant to absorb and retain large amounts of water. Hydrogels have emerged as promising wound dressing materials because they can fill irregular defects, provide a moist wound environment, serve as a barrier to microorganisms, and deliver therapeutic agents to the injury sites (Li et al. 2016, *Nature Reviews Materials* 1:1-17; Memic et al. 2015, *Biomed Mater* 11:014104). Additionally, they are typically formed from aqueous solution, which prevents denaturation and aggregation of the loaded drugs upon exposure to organic solvents. In particular, natural polymer-derived hydrogels have been highly pursued in wound healing applications due to their intrinsic biocompatibility, biodegradability, hemostatic property, antibacterial activity, and stimulation of wound healing.

Chitin and lignin are widely available and annually renewable natural polymers from food and agricultural bio-wastes that can be made into gels. Among them, chitin is a polysaccharide consisted of a long chain of N-Acetyl-glucosamine. It is the second most extensively available natural polymer in the world as the foremost component of crustaceans' shell and fungi cell wall. Lignin, on the other hand, is a cross-linked phenolic biopolymer. It is abundantly available as a by-product of the pulp and paper industry. Annual global production of chitin is estimated to be about 100 billion tons, yet the commercialized amount of chitin is only 150,000 tons. Likewise, more than 300 billion tons of lignin are globally produced out of which only 2% is used to produce commercial products, and the rest of them are commonly used as fuel to obtain energy. These polymers have numerous interesting characteristics that make them attractive for biomedical applications (Danti et al. 2019, *Internat J Mol Sci* 20:2669). Chitin has moisturizing properties, super swelling capacity, and anti-inflammatory activity; and lignin has the ability to absorb UV and has antimicrobial activity (Morganti. 2016, *Internat J Biotech Wellness Industries* 5:121-127; Dong et al. 2011, *Industrial Crops & Products* 34:1629-1634; Benhabiles et al. 2012, *Food Hydrocolloids* 29:48-56). Their combination as a composite gel could entrap and release many bioactive compounds, due to bivalency between positively charged chitin and negatively charged lignin. Additionally, chitin-lignin complexes can be used as adsorbents, due to their high adsorption capacity of numerous toxic metals such as lead, nickel and cadmium. Finally, recent studies showed that they could be used for intelligent drug delivery system, as they respond to pH and thermal stimuli (Sipponen et al. 2018, *ACS Sustainable Chem & Eng* 6:9342-9351; Jayakumar et al. 2012, *Carbohydrate Polymers* 87:2352-2356; Ding et al. 2014, *J Mat Chem B* 2:3050-3056).

However, there is a need for biomaterials that can both serve effectively as wound dressings and control the release of drugs to improve treatment outcomes. Furthermore, there is a need for localized delivery of antibiotics that targets only the wound area to fight infection, prevents drug resistance, and lowers the risk of adverse side effects. Previously, we have demonstrated the possibility of generating an ECM-like fibrous scaffold from chitin-lignin gels by electrospinning. Additionally, we reported significantly improved mechanical properties and antimicrobial performance by incorporating a biodegradable, tough elastomer polyglycerol sebacate (PGS) (Morganti et al. 2016, *Cosmetics* 3:41; Abudula, T. et al. The Effect of Poly (Glycerol Sebacate) Incorporation within Hybrid Chitin-Lignin Sol-Gel Nanofibrous Scaffolds. *Materials* 11, 451). However, those scaffolds quickly degraded in water-based media, providing only immediate, burst release of drugs. One of the approaches to overcome such challenges is the encapsulation of such gels by a hydrophobic shell polymer using coaxial electrospinning, which can also be used to generate high productivity follow fibers. A common hydrophobic polymer, polycaprolactone (PCL) is an aliphatic polyester that has been widely investigated for many biomedical applications including wound healing, owing to its easy processability and biocompatibility. The slower biodegradation rate and moderate hydrophobicity of PCL let it serve as a good barrier to retard fast dissolution of chitin-lignin (CL) gels in water. Although coaxial electrospinning for controlled drug delivery based wound dressing has been extensively studied, entrapping multicomponent gels with several natural and/or synthetic polymers and drugs by coaxial electrospinning has not been attempted.

SUMMARY OF THE INVENTION

The invention is a controlled-drug release based wound dressing scaffold, comprising core-shell nanofibers wherein a shell layer of the scaffold comprises polycaprolactone (PCL) having a thickness in the range of 5 to 100 nm, and a core layer of the scaffold comprises a mixture of chitin, lignin, polyethylene oxide (PEO) and polyglycerol sebacate (PGS). In one embodiment, the scaffold comprising core-shell nanofibers has an average diameter in the range of 100 to 500 nm. The shell layer of the scaffold is configured to provide a controlled rate of release of at least one drug, agent and/or bioactive nanoparticle loaded in the core layer of the scaffold. In one embodiment, the shell layer is configured to be adhesive to the skin or a wound surface.

In another embodiment, the invention is a method of preparing, by co-axial electrospinning, a controlled-drug release-based wound dressing scaffold, comprising shell-core nanofibers wherein a shell layer of the scaffold comprises polycaprolactone (PCL), and a core layer of the scaffold comprises a mixture of chitin, lignin, polyethylene oxide (PEO) and polyglycerol sebacate (PGS). The coaxial electrospinning encapsulates a chitin-lignin based hybrid gel with PCL. The shell layer of the scaffold is configured to provide a controlled rate of release of at least one drug, agent and/or bioactive nanoparticle loaded in the core layer of the scaffold.

In one embodiment, the shell layer of the scaffold is formed from a PCL solution in 9:1 chloroform and ethanol. In another embodiment, the PCL solution comprises a high molecular weight PCL within the range of 6-8% weight/volume, wherein the high molecular weight of the PCL is at least 70,000 daltons (Da).

In one embodiment, the core layer is formed by the mixture of an aqueous solution of chitin, lignin and PEO, and a PGS solution of ethanol. The aqueous solution can comprise at least 0.1 wt % of lignin, 30 wt % of an aqueous dispersion of chitin nanofibrils (2% w/v) and 7 wt % of PEO. In one embodiment, the volume ratios of the mixture of the aqueous solution of chitin, lignin and PEO, and the PGS solution in ethanol are in the range of 100/0 to 85/15.

The shell-core nanofibers have an average diameter in the range of 100 to 500 nm, and the shell typically has a thickness in the range of 5 to 100 nm. In one embodiment, the shell-core nanofibers have an average diameter in the range of 150 to 250 nm, and the shell has a thickness in the range of 10 to 30 nm.

In one embodiment of the method of preparing the scaffold, the core-shell nanofiber is produced by coaxial electrospinning the PCL solution at a shell feed rate in the range of 0.4 to 0.7 mL/hr, and a mixture of an aqueous solution of chitin, lignin and PEO and a PGS solution in ethanol at a core feed rate in the range of 0.1 to 0.3 mL/hr. The co-axial electrospinning is typically performed at 18 kV of voltage, having a needle-to-collector distance in the range of 12 cm to 14 cm.

In one embodiment, the controlled-release wound dressing scaffold of the invention comprises one or more bioactive nanoparticle (NP) and/or one or more water/ethanol soluble drugs or agents. The bioactive nanoparticle can be antimicrobial metal/metal oxides made of a material selected from the group consisting of silver, copper oxide and zinc oxide, but other materials are contemplated. Typically, a plurality of NPs is encapsulated within the scaffold in one embodiment of the invention. In another embodiment, the water/ethanol soluble drug is an antibiotic. In another embodiment, the shell or core layer comprises at least one of oxygen-releasing peroxides such as calcium peroxide ($CaO_2$), magnesium peroxide ($MgO_2$), hydrogen peroxide ($H_2O_2$), manganese dioxide, or sodium percarbonate (($Na_2CO_3)_2$) to overcome the oxygen supply shortages during the wound treatment. In another embodiment, the core layer comprises water-soluble antioxidants selected from the group consisting of vitamin C, glutathione and uric acid, and the core layer is formulated to inhibit oxidative damage of skin tissue.

In yet another embodiment, the shell layer or the core layer comprises at least one growth factor or peptide mimetic of a growth factor selected from the group consisting of epidermal growth factor, fibroblast growth factor and vascular endothelial growth factor, and the selected growth factor is able to stimulate tissue growth in and around the wound. Additional growth factors are contemplated and may be chosen based on a variety of factors, including cell types of the skin or wound area to be treated. In some embodiments, the shell layer is configured to provide adhesion to the skin or a wound surface.

In another embodiment, the invention is a method of treating a wound with controlled-release wound dressing in a subject in need thereof, comprising the steps of electrospinning the controlled-release wound dressing, comprising shell-core nanofibers, wherein a shell layer of the scaffold comprises polycaprolactone (PCL), and a core layer of the scaffold comprises a mixture of chitin, lignin, polyethylene oxide (PEO) and polyglycerol sebacate (PGS), during which the shell-core nanofiber is loaded with a therapeutically effective amount of at least one bioactive agent selected from the group consisting of an antibiotic, a bactericidal nanoparticle, an oxygen-releasing compound, an antioxidant agent and a growth factor, and contacting a wound with the controlled-release wound dressing for a suitable length of time, wherein the at least one bioactive agent is released from the scaffold at a controlled rate. The bioactive agents that may be used include antibiotics, antimicrobial nanoparticles, oxygen-releasing agents, antioxidants and growth factors or peptide mimetics of growth factors. In some embodiments of the method of treatment, the scaffold is optionally configured to adhere, at least temporarily, to the skin or surface of a wound. The dressing is left in place for a suitable length of time to promote healing of the wound or skin region of interest.

Other features and advantages of the present invention will be set forth in the description of the invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The accompanying drawings, which are incorporated in and constitute a part of this specification, illustrate embodiments of the invention and, together with a general description of the invention given above, and the detailed description is given below, serve to explain the invention.

DETAILED DESCRIPTION

Figure 1:
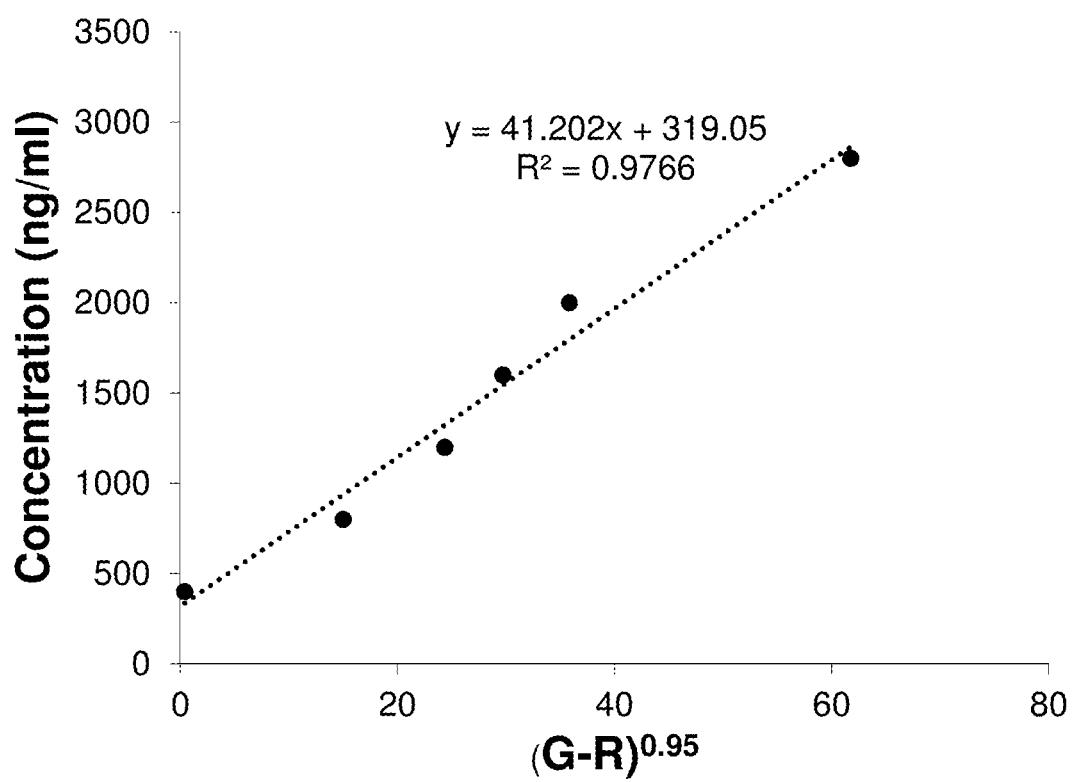
FIG. 1 shows the numerical correlation between MB concentration and green-red channel intensity difference in the solution.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

The invention is a controlled-drug release scaffold, comprising core-shell nanofibers wherein a shell layer of the scaffold comprises polycaprolactone (PCL) having a thickness in the range of 5 to 100 nm, and a core layer of the scaffold comprises a mixture of chitin, lignin, polyethylene oxide (PEO) and polyglycerol sebacate (PGS). In one embodiment, the scaffold comprising core-shell nanofibers has an average diameter in the range of 100 to 500 nm. The shell layer of the scaffold is configured to provide a controlled rate of release of at least one drug, agent and/or bioactive nanoparticle loaded in the scaffold. In one embodiment, the shell layer is configured to be adhesive to the skin surface or a wound. When thus loaded, the scaffold provides a sustained and continuous release of a drug, agent or bioactive nanoparticle to the local area of the skin surface or wound.

In another embodiment, the invention is a method of preparing, by co-axial electrospinning, a controlled-drug release wound dressing scaffold, comprising core-shell nanofibers wherein a shell layer of the scaffold comprises polycaprolactone (PCL), and a core layer of the scaffold comprises a mixture of chitin, lignin, polyethylene oxide (PEO) and polyglycerol sebacate (PGS). The coaxial electrospinning encapsulates a chitin-lignin based hybrid gel with PCL. The shell layer of the scaffold is configured to provide a controlled rate of release of at least one drug and/or bioactive nanoparticle loaded in the core layer of the scaffold. The drug may be water/ethanol soluble, such as an antibiotic or hydrophobic, such as a steroid hormone.

As used herein, the terms "core-shell" and "shell-core" are used interchangeably to refer to the structure of the nanofiber of the wound dressing scaffold of the invention. The nanofiber is coaxially electrospun from two solutions, resulting in a concentric two-layered fiber. The shell-core nanofibers have an average diameter in the range of 100 to 500 nm, and the shell typically has a thickness in the range of 5 to 100 nm. In one embodiment, the shell-core nanofibers have an average diameter in the range of 150 to 250 nm, and the shell has a thickness in the range of 10 to 30 nm.

As used herein, the term "coaxially electrospinning" is used to refer to a modification of the conventional electrospinning process involving the arrangement of multiple solution feed systems to simultaneously electrospin two or more polymer solutions from coaxial capillaries. Compared with surface modification, which modifies only the surface of the scaffolds, coaxial and emulsion electrospinning can load biological signals throughout the whole structure of the scaffolds. Furthermore, loaded drugs, nanoparticles and/or growth factors/mimetics can undergo sustained released for a controllable time.

As used herein, the terms "loaded" and "encapsulate" are used interchangeably to refer to the process of adding or incorporating a substance, which may be a therapeutic drug, agent and/or bioactive nanoparticle, into the nanofiber of the invention. A substance may be loaded into the shell layer, the core layer, or both layers of the nanofiber. As will be made clear in the Examples of the invention, the drug, agent and/or nanoparticles are added to one or both solutions used for electrospinning the nanofiber, and thus are incorporated into the nanofiber itself. The choice of layer for loading may be made on the basis of hydrophobicity or solubility of the selected substance in one solution or the other. Alternatively, the choice may be made based on the preferred rate of release. For example, in some embodiments, the selected substance is released at a slower rate when loaded into the inner core layer. In one embodiment, these can be mixed into the core solution and incorporated into the core layer of nanofiber as it is produced. In another embodiment, at least two different agents, drugs, or NPs are loaded, with one in the inner core layer and the other in the outer shell layer. In any case, the final product is loaded with at least one active ingredient, such as a drug, oxygen-releasing compound, antioxidant, growth factor or NP, in at least one layer.

In one embodiment, the shell layer of the scaffold is formed from a PCL solution in 9:1 chloroform and ethanol. The PCL solution comprises a high molecular weight PCL within the range of 6-8% weight/volume, wherein the high molecular weight of the PCL is at least 14,000 Da and up to 140,000 Da. In one embodiment, the molecular weight of the PCL is 70,000 Da. In another embodiment, shell layer of the scaffold is formed from other biodegradable, hydropobic high molecular weight polymers such as poly(lactic acid) (PLA), poly(lactic-co-glycolic acid) (PLGA), polyhydroyalkanoate (PHA), polybutylene succinate (PBS) and polyurethane (PU).

As used herein, the term "scaffold" is used to refer to the drug delivery platform of the invention. The scaffold is the core-shell nanofiber that may be loaded with any drug and/or bioactive agent of choice. The PCL shell layer of the scaffold also provides the mechanism for the controlled release of an encapsulated drug and/or bioactive agent. The slower biodegradation rate and moderate hydrophobicity of PCL provide a good barrier to retard dissolution of chitin-lignin (CL) gels in water. Examples of the invention will demonstrate that the rate of release of exemplary drugs can be determined and is repeatable, thus providing a predictable dosage of a drug or bioactive agent.

In one embodiment, the core layer is formed by the mixture of a first solution, which is an aqueous solution of chitin, lignin and PEO, and a second solution, which is a PGS solution of ethanol. The aqueous solution can comprise at least 0.05 to 2.0 wt % of lignin, 25 to 100 wt % of an aqueous dispersion of chitin nanofibrils (2% w/v) and 7 to 10 wt % of PEO. In one embodiment, the aqueous solution can comprise at least 0.1 wt % of lignin, 30 wt % of an aqueous dispersion of chitin nanofibrils (2% w/v) and 7 wt % of PEO. The PGS solution can comprise 10 to 30 wt % of PGS in ethanol. In one embodiment, the volume ratios of the mixture of the aqueous solution of chitin, lignin and PEO, and the PGS solution in ethanol are in the range of 100/0 to 85/15.

The shell-core nanofibers have an average diameter in the range of 150 to 250 nm, and the shell typically has a thickness in the range of 10 to 30 nm In one embodiment of the method of preparing the scaffold, the core-shell nanofiber is produced by coaxial electrospinning the PCL solution at a shell feed rate in the range of 0.4 to 0.7 mL/hr, and a mixture of an aqueous solution of chitin, lignin and PEO and a PGS solution in ethanol at a core feed rate in the range of 0.1 to 0.3 mL/hr. The co-axial electrospinning is typically performed at 18 kV of voltage, having a needle-to-collector distance in the range of 12 cm to 14 cm.

After the nanofiber is electrospun and collected, the samples are kept for 2-3 days at room temperature for a natural drying and further stored under refrigeration at approximately 4° C. for future use. The scaffold is in the form of a flexible sheet, so it can be easily cut or reshaped according to the conditions for the desired application.

The one or more bioactive NP is made of an antimicrobial material selected from the group consisting of silver, copper oxide and zinc oxide. Reactive magnesium oxide nanoparticles and halogen ($Cl_2$, $Br_2$) adducts of these MgO particles are also known to have bactericidal properties against Gram-negative and Gram-positive bacteria as well as spores. The mechanisms of bacterial killing include the production of reactive oxygen species, cation release, biomolecule damages, ATP depletion, and membrane interaction. Typically, a plurality of the NPs are collectively encapsulated within the scaffold in one embodiment of the invention.

In another embodiment, the core or shell layer comprises oxygen releasing compounds made of peroxides, including magnesium peroxide, calcium peroxide and sodium percarbonate and hydrogen peroxide. They are some of the most suitable sources to produce oxygen within scaffolds, as they are relatively stable against decomposition during the electrospinning process. Meanwhile, at a tuned concentration, they can be utilized for wound healing or other biomedical applications due to their low toxicity. When they are exposed to an aqueous environment upon the body temperature, they react with water and release oxygen.

In another embodiment, at least one water/ethanol soluble drug is an antibiotic. While any antibiotic that is soluble in water and/or ethanol may be used, one of ordinary skill in the art would select an antibiotic that is predicted to be effective against a target organism infecting or suspected to be infecting a wound to be treated. Thus, one might first obtain an isolate of tissue or a tissue discharge to be cultured to identify the infective organism and determine its sensitivity to various antibiotics. Commonly used antibiotics include amoxicillin, doxycycline, cephalexin, ciprofloxacin, clindamycin, metronidazole, azithromycin, sulfamethoxazole, trimethoprim, clavulanate and levofloxacin, and any of the many derivatives thereof. This list is not limiting since many other antibiotics not listed herein are water/ethanol soluble and may be found appropriate for use. The benefit of applying a local antibiotic will also be apparent to one of ordinary skill in the art, since the effects will be most highly concentrated within the wound and surrounding tissues, thus limiting exposure of sensitive organ systems and microbiomes known to be damaged by chronic or even transient exposure to certain antibiotics.

In another embodiment, the core layer comprises water-soluble antioxidants selected from the group consisting of vitamin C, glutathione and uric acid, and the core layer is formulated to inhibit oxidative damage of skin tissue. Antioxidants such as polyphenols, vitamins, and carotenoids are organic compounds mainly extracted from natural sources and are involved in boosting the host-defense system as scavengers of reactive oxygen species, thereby contributing to the body's antibacterial properties.

In yet another embodiment, the core layer comprises at least one growth factor or growth factor peptide mimetic, such as epidermal growth factor, fibroblast growth factor and vascular endothelial growth factor, and the selected growth factor is able to stimulate tissue growth in and around a wound to promote healing. A growth factor is a naturally occurring substance capable of stimulating cell proliferation, wound healing, and cellular differentiation of some cell types. Growth factors are also important for regulating a variety of other cellular processes. A naturally-occurring growth factor is typically a secreted protein that may be isolated and purified for use, but recombinant growth factors or "biosimilars" are also suitable for use in the invention, as are peptide mimetics that are small molecules that typically include bioactive moieties of a growth factor (i.e., binding motifs and/or catalytic sites). Use of other growth factors is contemplated, including but not limited to angiopoietin, bone morphogenetic proteins, ciliary neurotrophic factor, leukemia inhibitory factor, interleukin family members (such as IL-6), colony-stimulating factors (GM-CAF, M-CSF and G-CSF), epidermal growth factor, ephrin family members, erythropoietin, fibroblast growth factor family members, growth differentiation factor-9, hepatocyte growth factor, hepatoma-derived growth factor, insulin-like growth factors, keratinocyte growth factor, macrophage-stimulating protein, myostatin, neuregulin family members, neurotrophin family members, platelet-derived growth factor, renalase, thrombopoietin, transforming growth factors, tumor necrosis factor-alpha, vascular endothelial growth factor, and any Wnt signaling pathway members.

In some embodiments, the scaffold is configured to provide adhesion to the skin or a wound surface. One way to do this is to functionalize the outer shell layer to make it adhesive. For example, polydopamine (immersed in either 0.2 or 2 mg/mL dopamine HCl (10 mM) in Tris buffer (pH 8.5) for either 0.5, 4, or 72 h) could be used to treat the outer PCL shell layer such that the polydopamine would interact with the skin and make the surface adhesive.

In another embodiment, the invention is a method of treating a wound with controlled-release wound dressing in a subject in need thereof, comprising the steps of:

electrospinning the controlled-release wound dressing in the form of a scaffold, comprising shell-core nanofibers, wherein a shell layer of the scaffold comprises polycaprolactone (PCL), and a core layer of the scaffold comprises a mixture of chitin, lignin, polyethylene oxide (PEO) and polyglycerol sebacate (PGS), loading the scaffold with a therapeutically effective amount of at least one bioactive agent selected from the group consisting of an antibiotic, a water-soluble antioxidant, a bactericidal nanoparticle, and a growth factor, and contacting a wound with the controlled-release wound dressing for a suitable length of time, wherein the at least one bioactive agent is released from the scaffold at a controlled rate.

In some embodiments of the method of treatment, the scaffold is optionally configured to adhere, at least temporarily, to the skin or surface of a wound. The effects of at least one of an antibiotic, antioxidant, oxygen-releasing compound, bactericidal nanoparticle and/or growth factor are restricted to the local area of application, thus limiting side effects of systemic administration of these agents. This is particularly advantageous when treating a chronic wound, such as diabetic ulcers and any other wound that is slow to heal.

Previously, we have demonstrated the possibility of generating an ECM-like fibrous scaffold from chitin-lignin gels by electrospinning. Additionally, we reported significantly improved mechanical properties and antimicrobial performance by incorporating a biodegradable, tough elastomer polyglycerol sebacate (PGS) (Morganti et al. 2016, *Cosmetics* 3:41; Abudula, T. et al. The Effect of Poly (Glycerol Sebacate) Incorporation within Hybrid Chiting Lignin Sol-Gel Nanofibrous Scaffolds. Materials 11, 451, (2018). However, those scaffolds quickly degraded in water-based media, providing only immediate, burst release of drugs. One of the approaches to overcome such challenges is the encapsulation of such gels by a hydrophobic shell polymer using coaxial electrospinning, which can also be used to generate high productivity follow fibers (Duan et al. 2017, *Biomacromolecules* 18:3215-3221; Nguyen et al. 2015, *Int. J. Pharm.* 439:296-306; Kuo, Ting-Yun, et al. "Fabrication and application of coaxial polyvinyl alcohol/chitosan nanofiber membranes." Open Physics 15.1 (2017): 1004-1014). A common hydrophobic polymer, polycaprolactone (PCL) is an aliphatic polyester that has been widely investigated for many biomedical applications including wound healing, owing to its easy processability and biocompatibility. The slower biodegradation rate and moderate hydrophobicity of PCL let it serve as a good barrier to retard fast dissolution of chitin-lignin (CL) gels in water (Abdal-Hay, Abdalla, et al. "Rapid fabrication of highly porous and biocompatible composite textile tubular scaffold for vascular tissue engineering." European Polymer Journal 96 (2017): 27-43; WO2016207808A1 by Massey-Brooker et al.). The nanofibers of the invention are formulated to maintain their structure for at least as long as they are used for the controlled-release of a drug or other bioactive agent or NP. Since the scaffolds are made of biodegradable polymers, they eventually degrade with the wound and do not need to be physically removed.

Before exemplary embodiments of the present invention are described in greater detail, it is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following Examples provide exemplary designs and methods for fabricating and using microgrippers of the invention. These Examples describe materials and methods for using embodiments illustrated in FIGS. 1-11. Additional details about the figures can be found in the section entitled "Brief Description of the Drawings".

The following Examples demonstrate the morphological, chemical, thermal, and mechanical properties of the core-shell fibrous scaffold. Drug release characteristics of the core-shell fibrous scaffold were assessed using methylene blue (MB) as a model drug. Penicillin/streptomycin (PS)-loaded substrates were used in Examples of the effectiveness of the drug release against gram-positive and/or gram-negative bacterial strains. Finally, the biocompatibility of the drug-loaded platform was assessed using bone marrow-derived mesenchymal stem cells (BM-MSCs) and NIH 3T3 cells. Taken together, these examples demonstrate that this biomaterial platform has many advantages that are significant improvements when compared to existing wound healing and dressing products.

Materials and Methods

Materials and Solution Preparation

Chitin nanofibrils in the form of 2% water suspension, bio-lignin (CIMV, France) and PEO were provided by Nanoscience Centre (MAVI, Italy). All the other chemicals were purchased from Sigma-Aldrich (St. Louis, Mo., USA). Polyglycerol sebacate (PGS) was prepared using the polycondensation of glycerol and sebacic acid in a 1:1 ratio as reported previously (Wang et al. 2002, *Nat Biotechnol* 20:602-606).

The hybrid solution was prepared by mixing CL sol-gel solution and PGS solution in a 9:1 volume ratio, with gently stirring for 30 minutes. Details of CL based sol-gel solution and PGS solution preparation have been reported in earlier studies (Sipponen et al. 2018, *ACS Sustainable Chem & Eng* 6:9342-9351). Briefly, 30 wt % of chitin nanofibrils suspension, 0.1 wt % of bio-lignin, and 7 wt % of PEOX were dispersed into 62.9 wt % deionized water; pH of the mixture was raised to 10.5 using 0.1 M of NaOH. Then, the mixture was shielded and kept on a magnetic stirrer for 48 h to obtain a uniform CL sol-gel solution. PGS solution was prepared by dissolving 25% (w/v) of PGS in ethanol under stirring for half hours. 8% (w/v) of PCL was dissolved in chloroform and ethanol (9:1) by stirring at room temperature for 3 hours.

Coaxial Electrospinning

NANON-01A Electrospinning System (MECC, Fukuoka, Japan) was adapted for coaxial electrospinning under a normal lab atmosphere with 63% humidity. The PCL solution was delivered to the outer layer of Ultra-thin coaxial spinneret (NANON Supply, MECC, Fukuoka, Japan) by the system-provided syringe pump using Teflon tube (Cole-Parmer Instrument Company; Vernon Hills, Ill., USA) at 0.5 ml/h of feed rate. An extensional syringe pump (KDS 100, KD Scientific Inc, USA) connected with 20 cm of Teflon tube was used to deliver the hybrid solution into a 27-gauge blunt metallic needle (NANON Supply, MECC, Fukuoka, Japan) at 0.2 ml/h of feed rate. Then the double layer solution was electrically stretched at 18 kV of voltage over 150 mm of distance. For individual hybrid fiber and PCL fiber preparation, the feed rate was fixed at 0.3 ml/h and 0.9 ml/h respectively. During the electrospinning, the needle was allowed to axially sway in an 8 cm range with 10 cm/s of moving speed, and the formed fibers were collected on a stationary flat aluminum sheet. Electrospinning was performed for 4 hours in all cases, and the needle tip was automatically cleaned every 5 minutes. The collected samples were dried for 48 hours at room temperature before any characterization test.

Characterization

The microstructure of the electrospun membranes was observed using JSM 7600F scanning electron microscopy (FESEM, JEOL, Japan). The fiber size distribution was determined using a newly developed digital image processing method in "Matlab", which generates a statistically reliable Gaussian distribution curve with punctilious density estimation. Details of the image processing method can be found elsewhere (Abudula, Tuerdimaimaiti et al. "Study of electrospinning parameters and collection methods on the size distribution and orientation of PLA/PBS hybrid fiber using digital image processing." Journal of nanoscience and nanotechnology 18.12 (2018): 8240-8251).

Layered structure of core-shell fiber was observed by JEM-2100 F high-resolution transmission electron microscope (FETEM, JEOL, Japan). The fiber was electrospun for 45 seconds on a carbon holey grid for TEM sample preparation. Shell thickness of the core-shell fiber was estimated using a direct measuring method on "Image J" software, based on a 12000-magnified TEM image. 100 data were obtained from different positions of the fiber to determine the mean shell thickness of the fiber.

Bulk composition of the fibrous mesh was dissected based on Attenuated Total Reflected Fourier transform infrared spectroscopy (ATR-FTIR, Thermo Fisher Scientific, MA, USA) in 400-4000 $cm^{-1}$ of wavenumber range. The surface composition of the prepared fibers was analyzed by X-ray Photoelectron Spectroscopy (XPS) measurements using a surface nano analysis system (SPECS GmbH, Germany). SPECS XR-50 with Mg—Kα at1283.6 eV was used to irradiate the sample. 284.6 eV corresponding to the C—C bond was used as a reference to determine the binding energies of elements contained in the sample.

Differential scanning calorimetry (DSC-60, MICRO DSC3 EVO; Setaram Inc, USA) was used to examine the thermal behavior of the samples. Endothermal and exothermal curves were obtained by heating the fibrous sheets up to 180° C., then cooling down to 25° C. Nitrogen 35 ml/min of feed rate was used as a purgent. Uniaxial tensile test measurement for the fibrous mat (4 cm in length and 1 cm in width) was conducted using a universal tensile machine (Lloyd Instruments Ltd., Bognor Regis, UK). The tensile curve was obtained by stretching the sample at 10 mm/min extension speed, and the sample thickness was measured by an electronic caliper.

Biodegradation and Drug Release

In vitro biodegradation test and methylene blue (MB) release test was performed by immersing 20 mg of the electrospun fibrous mats into 5 ml of phosphate buffer saline (PBS) at 37.5° C. MB was incorporated into the core solution at 2 mg/ml of concentration before electrospinning. The weight of the mats over a different period of time was measured by micro balance (0.01 mg precision), and a UV test was performed for the solution using a UV-Vis spectrophotometer (NanoDrop™ 2000, Thermofisher Scientific, USA). The color change of the solution was also recorded by using a digital camera. The image processing technique in Matlab software (R2017a) was used to analyze the MB release behavior in the fibrous mat. A carefully cropped solution image matrix was divided into red, green and blue (RGB) channels, and the average intensity of each channel was calculated. Finally, the concentration of MB in the solution was correlated with the average intensity of the RGB channel by the following equation (See Table 1 and FIG. 1):

$$C_{MB}=41.202(G-R)^{0.95}+319.05, (R^2=0.9766) \quad (1)$$

where $C_{MB}$ is the concentration of MB in the solution (ng/ml), G and R are the average intensity of the green and red channels.

TABLE 1

Average intensity change between red, green and blue channel at different concentration of methylene blue

| Methylene blue Concentration | The average intensity of channels | | | |
|---|---|---|---|---|
| | Red (R) | Green (G) | Blue (B) | $(G - R)^{0.95}$ |
| 400 ng/ml | 232.98 | 233.37 | 234.17 | 0.412116 |
| 800 ng/ml | 165.28 | 182.60 | 188.92 | 15.01519 |
| 1200 ng/ml | 170.42 | 199.26 | 209.18 | 24.3768 |
| 1600 ng/ml | 198.57 | 234.1 | 230.91 | 29.71031 |
| 2000 ng/ml | 141.55 | 184.81 | 180.38 | 35.83399 |
| 2800 ng/ml | 71.59 | 148.34 | 151.49 | 61.77426 |

Antibacterial Activity and Biocompatibility

Loading of PS was achieved by introducing 1000 unit/ml of penicillin and 1000 µg/ml of streptomycin in the core solution, and electrospinning at similar condition mentioned above. Isolated colonies of E. coli strain and S. aureus strain were placed in lysogeny broth (LB) media containing ampicillin (100 µg/mL$^{-1}$) at 37° C., and cultured overnight. Then 200 µL of cultured strains were spread on the LB-agar plate surface containing 100 µg/ml of ampicillin to get a mat of bacteria. Disks of hybrid and core-shell fibrous scaffold (three for each) containing PS were placed on the top of bacterial strain and incubated overnight. Non drug-loaded scaffolds were used as control.

The biocompatibility of PS loaded scaffolds was tested by culturing bone marrow-derived mesenchymal stem cells (BM-MSCs). Sterilized PS-loaded scaffolds (~2 mg dry weight) were cut and put into a 48-well culture plate. These scaffolds were then seeded with BM-MSCs (1×10$^4$ cells/well), and the culture plate incubated under regular cell culture conditions in a 5% $CO_2$ incubator at 37° C. A reagent kit for 3-(4,5-dimethylthiazolyl-2)-2,5-diphenyltetrazolium bromide (MTT) was used as cell proliferation assay. An aliquot of 0.5 mg/mL MTT reagent was introduced to the cells in culture and the culture plate was incubated in a 5% $CO_2$ incubator until purple formazan precipitate was formed. Then 100 µl of the detergent reagent was used to dissolve the formazan in the dark for 2 h. The optical density of the formazan was measured by a microplate reader (SpectraMax® i3, San Jose, USA) at 570 nm of wavelength using a 630 nm wavelength as a reference.

The viability and proliferation rate of NIH 3T3 cells were quantified by measuring their metabolic activities using PrestoBlue™ Cell Viability Reagent (Invitrogen) 24 h after culturing with the samples and maintaining in complete growth media. At the 24 h time point, samples were incubated in a solution of 10% (v/v) of PrestoBlue™ reagent in growth media in the incubator at 37° C. for 1 hour. The fluorescence intensity of the solution was measured using a Cytation™ 5 Cell Imaging Multi-Mode Reader (Biotek, USA) at 540 nm (excitation)/600 nm (emission).

Statistical Analysis

Statistical analysis was performed in Origin (OriginPro 8.0, Origin Lab Inc., USA) using the One-way Analysis of variance (ANOVA) approach. Statistical significance at $p<0.05$ and $p<0.01$ is denoted by single and double asterisks, respectively.

Example 1

Figure 2:
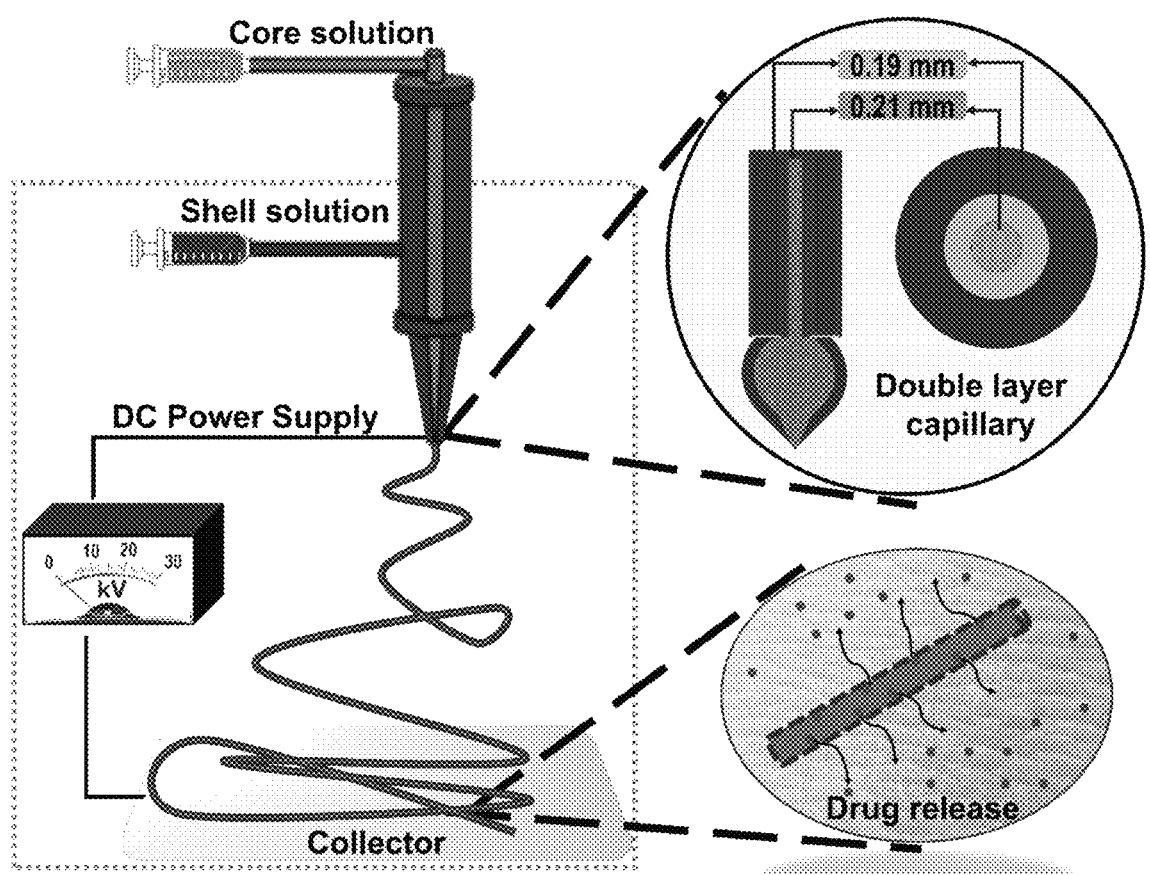
FIG. 2 shows a systematic representation of chitin-lignin (CL)-based hybrid fiber encapsulation by PCL using a coaxial electrospinning technique for sustained drug release.
Figures 3A, 3B, 3C, 3D, 3E, 3F:
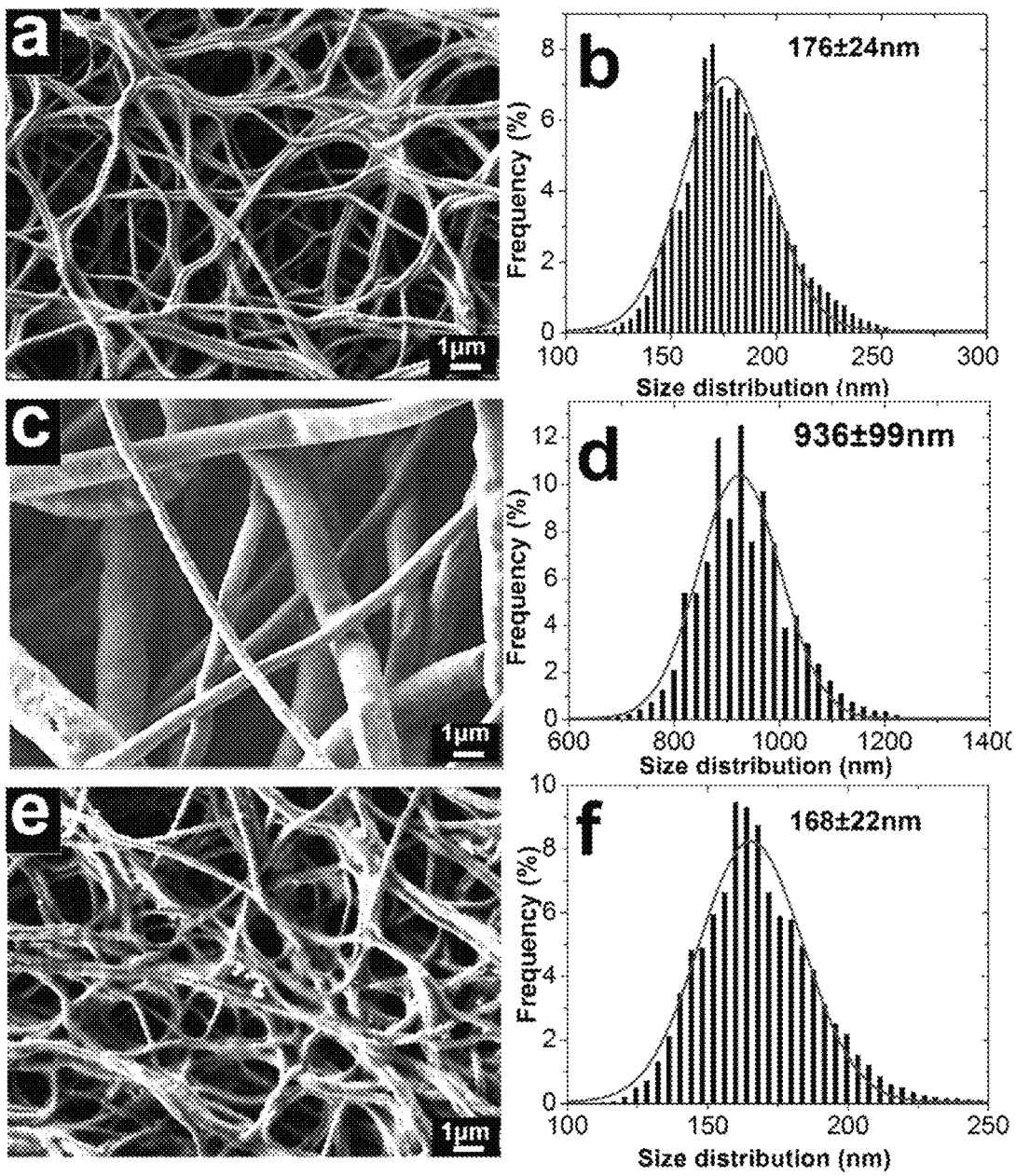
FIGS. 3A-3F show representative SEM micrographs and fiber size distribution for three fiber types: hybrid fiber in 3A and 3B, PCL fiber in 3C and 3D, and core-shell fiber in 3E and 3F, respectively.

The fabrication process of core-shell nanofibers using coaxial electrospinning is shown schematically in FIG. 2, which is a systematic representation of chitin-lignin (CL)-based hybrid fiber encapsulation by PCL using coaxial electrospinning technique and theoretical assumption for its drug release behavior. A mixture of CL sol-gel solution and PGS solution in 9:1 volume ratio is used as a core solution, and PCL solution is used as a shell solution to produce the core-shell fiber. The core solution and shell solution are fed into separate coaxial chambers within a syringe. The coaxial spinneret configuration is made by inserting a 27 gauge needle (inner diameter: 0.21 mm; thickness: 0.105 mm) into a shell spinneret with 0.8 mm of inner diameter. The formation of double-layered Tailor's cone takes place from inner and outer droplets fed by different syringes in the presence of a high voltage electrical field generated by a DC power supply (Nguyen et al., supra). The Tailor's cone jet laterally stretches towards the collector and as the solvents evaporate it leads to the formation of an ultrathin core-shell fiber (Nguyen et al., supra; Reneker, Darrell H., and Alexander L. Yarin. "Electrospinning jets and polymer nanofibers." Polymer 49.10 (2008): 2387-2425). Both inner and outer solutions simultaneously experience the same electrical field during this process. Therefore, primary electrospinning parameters including feed rate, polymer concentration, voltage and the nozzle-collector distance need to be optimized and balanced for each solution (Diaz, Juan Esteban, et al. "Controlled encapsulation of hydrophobic liquids in hydrophilic polymer nanofibers by co-electrospinning." Advanced Functional Materials 16.16 (2006): 2110-2116.). Previously, 18 kV applied voltage was used when electrospinning sol-gel CL/PGS (hybrid fiber) solutions (Abudula, T. et al. The Effect of Poly (Glycerol Sebacate) Incorporation within Hybrid Chitin-Lignin Sol-Gel Nanofibrous Scaffolds. Materials 11, 451, (2018)). Similarly, 19.5 kV was applied voltage for electrospinning of a 10 wt % PCL solution using an in-house system to produce smooth nanofibers (Memic et al. 2017, *Nanomaterials* 7:63). Based on these results, the PCL concentration was decreased to 8 wt % for the current example in order to achieve stable electrospinning at 18 kV. When the product core-shell nanofibers are loaded with a drug or other bioactive agent, the drug release is controlled and sustained over a defined period of time.

In initial studies, controlling the feed rate during the coaxial electrospinning of core and shell solutions was crucial to achieve smooth core-shell fibers. When the feed rate of PCL solution is too high, the electrospinning process was not stable resulting in significant fusions of fibers. When the feed rate of PCL solution was too low or the feed rate of the CL/PGS solution was too high, resulting fibers were not effectively encapsulated by PCL. This would ultimately affect in vitro degradation and the controlled drug release. Another factor that had to be considered during electro spinning was the solvent evaporation rate. Specifically, the length of tubes that deliver the polymer solutions was optimized to prevent polymer precipitation and aggregation due to a mismatch between polymer solvent evaporation (i.e. chloroform, solvent for the shell polymer has a much higher vapor pressure than water, solvent for the core solution).

Example 2

Core-shell fibers were electrospun as disclosed in Example 1. SEM micrographs and the corresponding fiber size distribution curves of CL/PGS (hybrid), PCL and core-shell fibers are presented in FIGS. 3A-3F. A representative SEM micrograph and fiber size distribution are shown for hybrid fiber in FIGS. 3A and 3B, for PCL fiber in FIGS. 3C and 3D, and for core-shell fiber in FIGS. 3E and 3F, respectively.

The result shows the morphological and dimensional similarity of the core-shell fibers with the hybrid fibers alone. Although the mean size of PCL fibers is five times higher than the size of hybrid fibers, the produced core-shell fibers showed similar size distribution in comparison with the hybrid fibers alone. This implies that the core layer is the leading contributor to morphology and size distribution of the core-shell fibers. Without being bound by theory, this might be associated with the high electrical conductivity of the core solution (Yu, Jian H., Sergey V. Fridrikh, and Gregory C. Rutledge. "Production of submicrometer diameter fibers by two-fluid electrospinning." Advanced Materials 16.17 (2004): 1562-1566). In this example, 90% of the core solution was sol-gel CL solution and 10% was PGS. It was reported previously that the sol-gel CL solution has a conductivity of 7.8 milliSiemens (mS) (Morganti et al. 2016, *Chem Eng Trans* 47:61-66), which is significantly higher than the value for PCL solution, i.e., almost non-conductive at <0.04 microSiemens (µS) (Zhang et al. 2019, *Coatings* 9:84). Therefore, high surface charge density might exist that is derived from the core solution in our coaxial setup, which potentially promotes longer elongation of the Tailor cone jet and ultimately increases whipping and decreases fiber size (Reneker et al. 2000, *J Appl Phys* 87:4531-4547).

Example 3

Figures 4A, 4B, 4C:
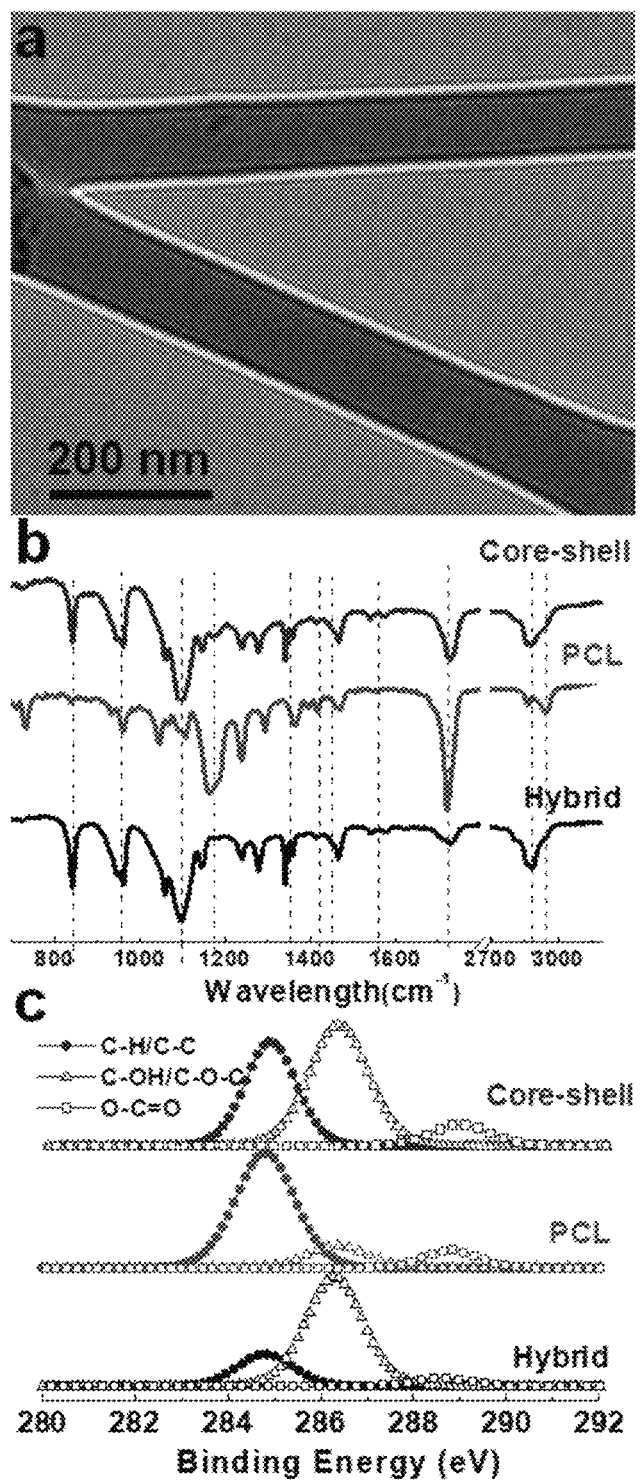
FIGS. 4A-4C show a TEM image of the core-shell fiber in 4A, representative FTIR spectra of the electrospun scaffolds in 4B, and deconvolved XPS spectra of carbon in the scaffolds in 4C.
Figures 5A, 5B, 5C:
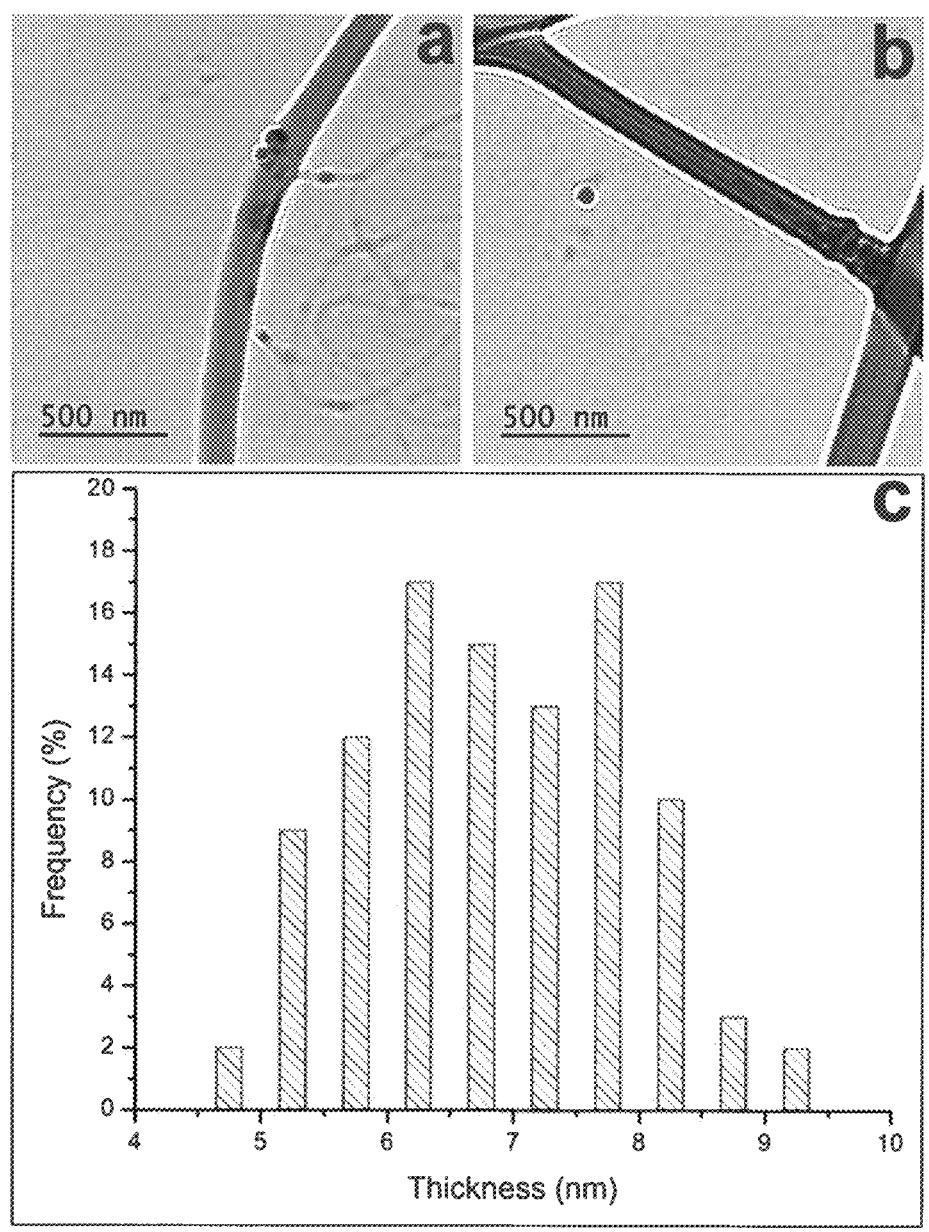
FIGS. 5A-5C show TEM images of the hybrid fiber in 5A and the core-shell fiber in 5B; with the calculated shell thickness distribution for the core-shell fiber in 5C.

To visualize the layered architecture of the core-shell fibers, TEM imaging was performed. From the TEM image, it can be observed that clear boundaries existed between core and shell layers, which confirms the effective encapsulation of hybrid fibers by PCL, as shown in FIG. 4A (core-shell fiber). The core solution not only contained several different polymers with 36.0 w.t % total polymer concentration but also the water was partially remained trapped in the core solution to yield a gelatinous fiber core. Namely, the density of the resulting core layer (~0.371 g/cm$^3$ without considering the trapped water) is at least 4 times higher than the shell layer one (0.916 g/cm$^3$). In addition, the slower evaporation rate of the core solvents and its high conductivity increases the inner/core layer thickness when compared to the outer/shell layer during electrospinning (Reneker et al, supra; Li, Dan, et al. "Nanofibers of conjugated polymers prepared by electrospinning with a two-capillary spinneret." Advanced Materials 16.22 (2004): 2062-2066).

Chemical analysis of the electrospun fibers was performed using FTIR and XPS. The FTIR illustrates the bulk composition of the fibrous sheets, while XPS specifically provides their surface composition. Detailed analysis of the chemical composition of the hybrid and PCL fiber by FTIR has been reported in our earlier studies (Sipponen et al, supra; Memic et al, supra). The FTIR spectra of core-shell fiber appeared to be similar to that of the hybrid fiber, and only strong peaks of PCL such as peak at 1723 corresponding to carboxyl stretching (C=O) were noticeable. This emphasizes the dominance of core composition over shell in the core-shell fiber, as shown in FIG. 4C. Deconvoluted XPS spectra of Carbon for the different fibers showed that the spectra corresponded to single bonds between carbon and oxygen (C—O) much more intensely when compared to bonds between carbon and hydrogen (C—H) for the hybrid fibers. This indicates that the C—O bonds are highly dominant in the fiber. On the other hand, the peak intensity of the C—H spectra was higher than the C—O spectra in the case of PCL fibers, showing the dominance of the C—H bond rather than the C—O bond. Comparatively, the deconvoluted XPS spectra of carbon in the scaffolds of core-shell fiber indicate a combination of peaks from both the shell and core layers, shown in FIG. 4D. The typical depth of XPS analysis is generally accepted to be up to 10 nm (Mimura et al. 2010, *Nature Physics* 6:122-125). The fiber shell layer was thinner compared to the core layer (FIG. 5), which could be attributed to the concentration difference between the core solution and the shell solutions. In general, the shell thickness of the core-shell fibers being <10 nm is in agreement with the characterization by both TEM and XPS.

Example 4

Figures 6A, 6B:
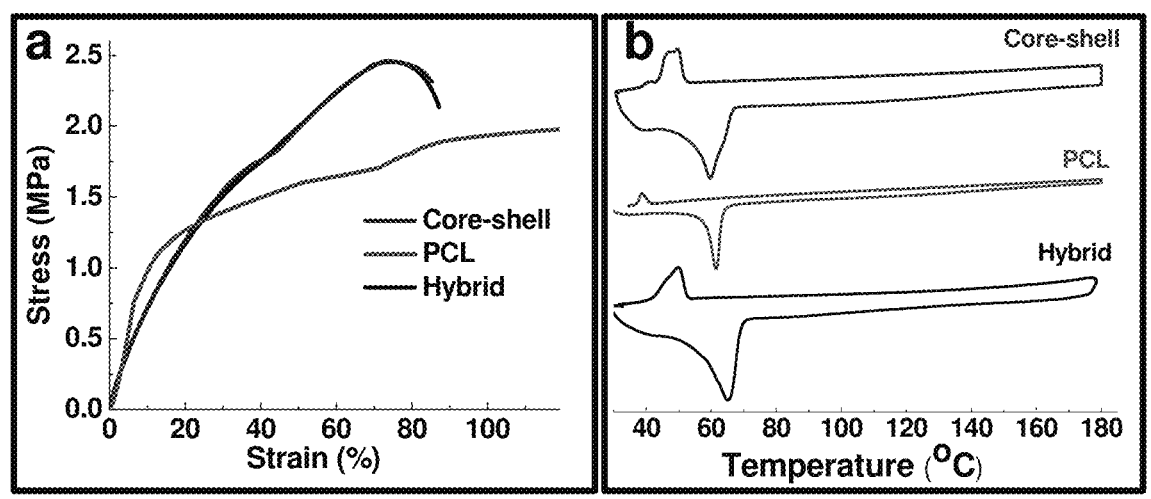
FIGS. 6A and 6B show the stress-strain curve of electrospun scaffolds in 6A and the DSC curve of the electrospun scaffolds in 6B.
Figure 7:
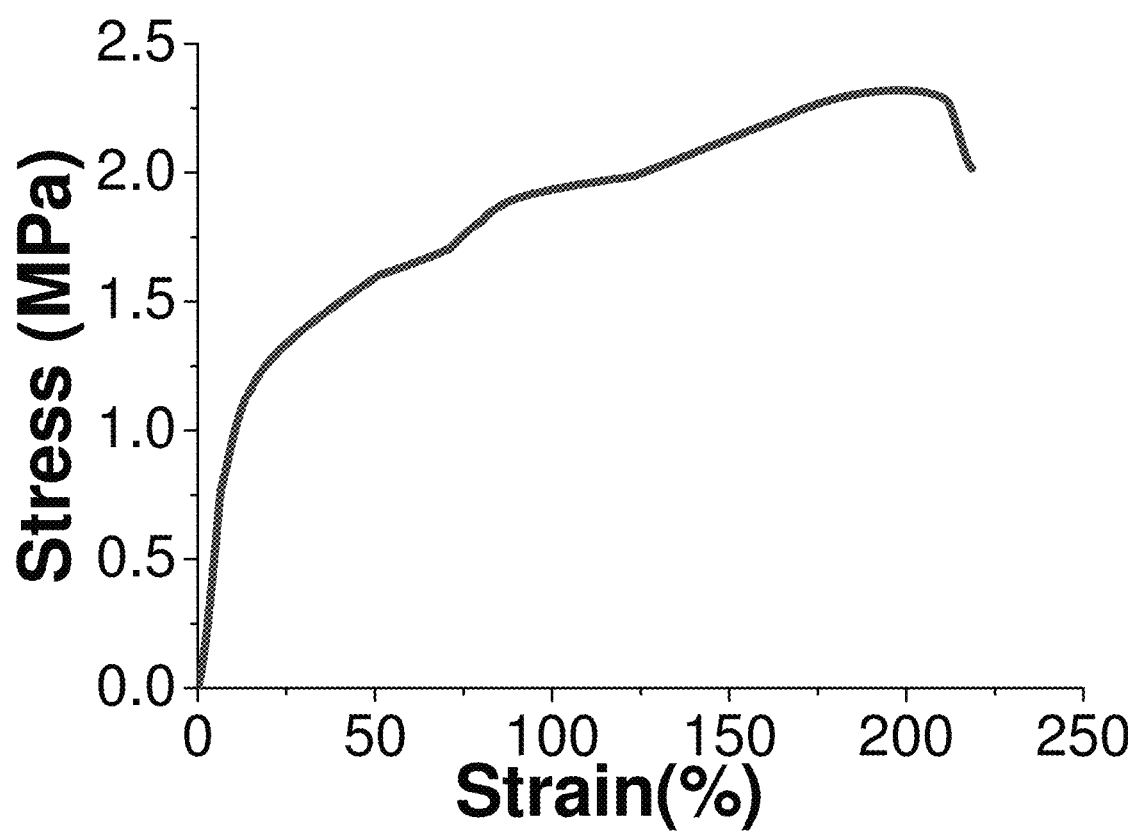
FIG. 7 shows a representative stress-strain curve for the electrospun PCL scaffold.

Considering that PCL formed a very thin outer layer, it did not considerably influence the mechanical behavior of core fibers, as shown in FIG. 6A for the stress-strain curve and 6B for the DSC curve of the electrospun scaffolds. Generally, PCL fibers exhibited similar tensile strength, but much higher flexibility compared to the hybrid fibers (FIG. 7). No significant change in mechanical compliance was observed for the core-shell fibers, as shown in FIG. 6A. FIG. 6B of DSC measurement shows that the endothermic peak of core-shell fibers was a combination of hybrid and PCL fiber peaks and represents melting points of PEO (present in the core solution) and PCL, respectively. Two separate exothermic peaks were observed for core-shell fibers in the cooling process. This might be due to the melting of the core-shell fiber and phase separation during heating, with two distinct crystallizations observed for PEO and PCL in the fibrous mesh. The results of Example 4 indicate insignificant effects of PCL encapsulation on thermal transition and mechanical behavior of the CL based hybrid fibrous scaffold.

Example 5

Figures 8A, 8B, 8C, 8D:
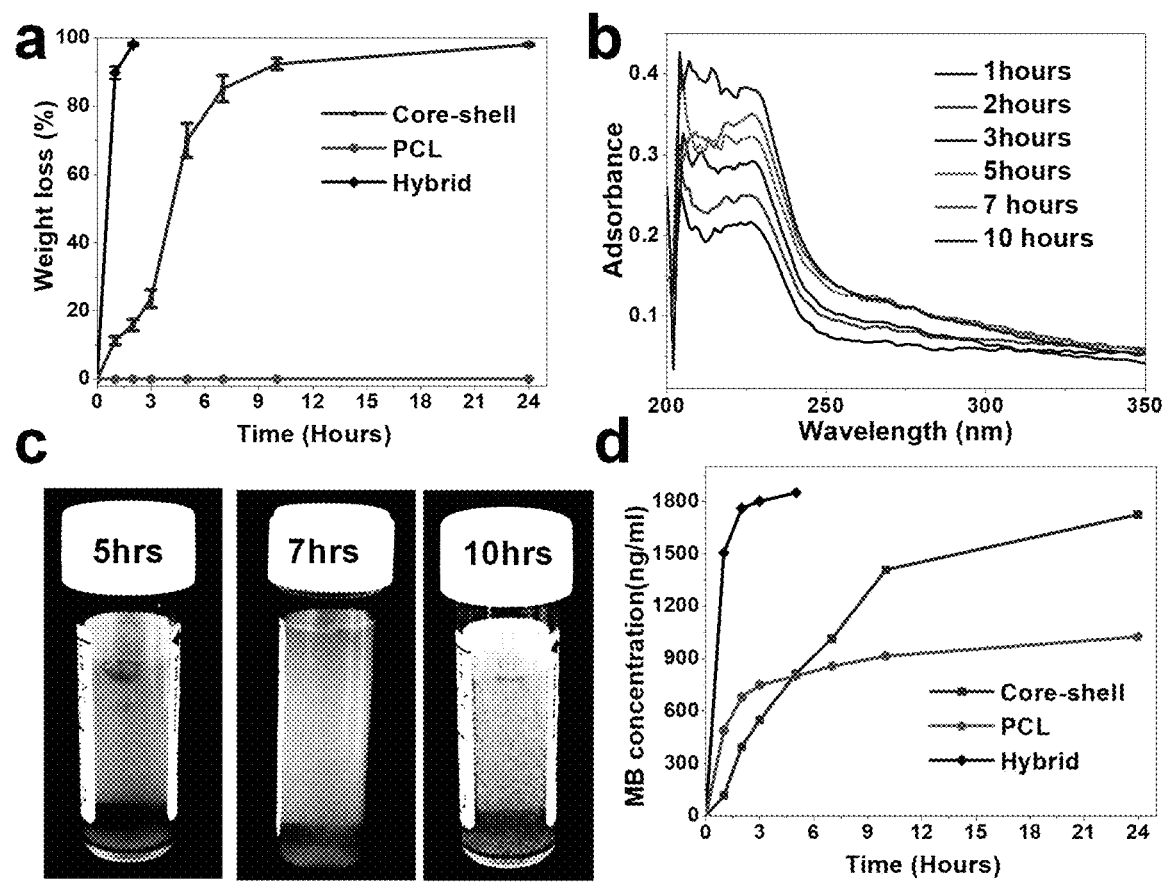
FIGS. 8A-8D show the weight change of the electrospun fiber under PBS, pH=7.4. 8A shows UV spectra change and representative color change of the PBS solution after immersing the core-shell fibrous sheet in 8B and 8C, and methylene blue release profile from the electrospun scaffolds in 8D.

The presence of the PCL shell significantly retarded the dissolution rate of the hybrid fiber in PBS media. The CL fibers without PGS dissolved very quickly (i.e. in less than 15 minutes), and PGS incorporation extended the fiber shelf life for up to 2 hours, measured by weight change of the electrospun fiber under PBS (pH=7.4), as shown in FIG. 8A. However, the core-shell fibers appeared to have a three-stage dissolution profile, and shelf life lasted for more than 24 hours. The dissolution rate of the core-shell fiber in the initial 3 hours was slow, then rapid dissolution occurred in the next 2 hr, and it slowed down again in the last stage. This is a common phenomenon for many biodegradable polymers, which could be associated with the diffusion effect of PBS through the hydrophobic PCL layer, the interfacial transaction between PBS and the core layer of the fiber, and molecular weight change of the individual polymers (Khatiwala, Vinay K., et al. "Biodegradation of poly (ε-caprolactone)(PCL) film by *Alcaligenes faecalis*." Journal of Polymers and the Environment 16.1 (2008): 61-67).

UV spectra of PBS media after immersing the core-shell fiber exhibited a broad absorbance in the range of 200-230 nm, and its intensity directly increased with immersion time, as shown in FIG. 8B, as measured UV spectra change in absorbance. Liu et al. (Liu, D., Wei, Y., Yao, P. & Jiang, L. Determination of the degree of acetylation of chitosan by UV spectrophotometry using dual standards. Carbohydr. Res. 341, 782-785, (2006)) suggested that N-acetylglucosamine and glucosamine residues in chitin were UV chromophoric, and they showed a broad, high extinction coefficient under 225 nm wavelength. According to Shende et al. (Shende, A., R. Jaswal, D. Harder-Heinz, A. Menan, & R. Shende. Integrated photocatalytic and microbial degradation of kraft lignin. *Cleantech*, 120-123 (2012)), unsaturated chains of lignin are capable of adsorbing UV light at about 210 nm wavelength. Accordingly, these results suggest that the dissolution of chitin and lignin mostly follows the overall dissolution of the core layer in core-shell fiber. Overall, the results imply the role of PCL shell layer coating on the CL based hybrid scaffold is to prevent burst release and provide a prolonged drug release profile.

Methylene blue (MB) as a model drug was used to examine the drug release behavior of the core-shell fibers. MB is a multifunctional therapeutic agent, and it has a century of medical practice history. MB could strongly inhibit nitric oxide, which abates endothelial function, restrains synaptic transmission, moderates immunity, and causes cell death by activating guanylate cyclase. MB is also a strong antioxidant, which can protect cells and tissues from the noxious effects of reactive oxygen species by competing with molecular oxygen for the electron transferred by xanthine oxidase. Additionally, activation, adhesion and aggregation of blood platelets can be also prevented by MB (Miclescu et al. 2010 *J Rom Anest Terap Int* 17:35-41). Moreover, MB has been also used as a photosensitizer in photodynamic therapy to positively modulate the vascular wound healing response (Salaris et al. 1991, *Biochem Pharmacol*).

Figure 9:
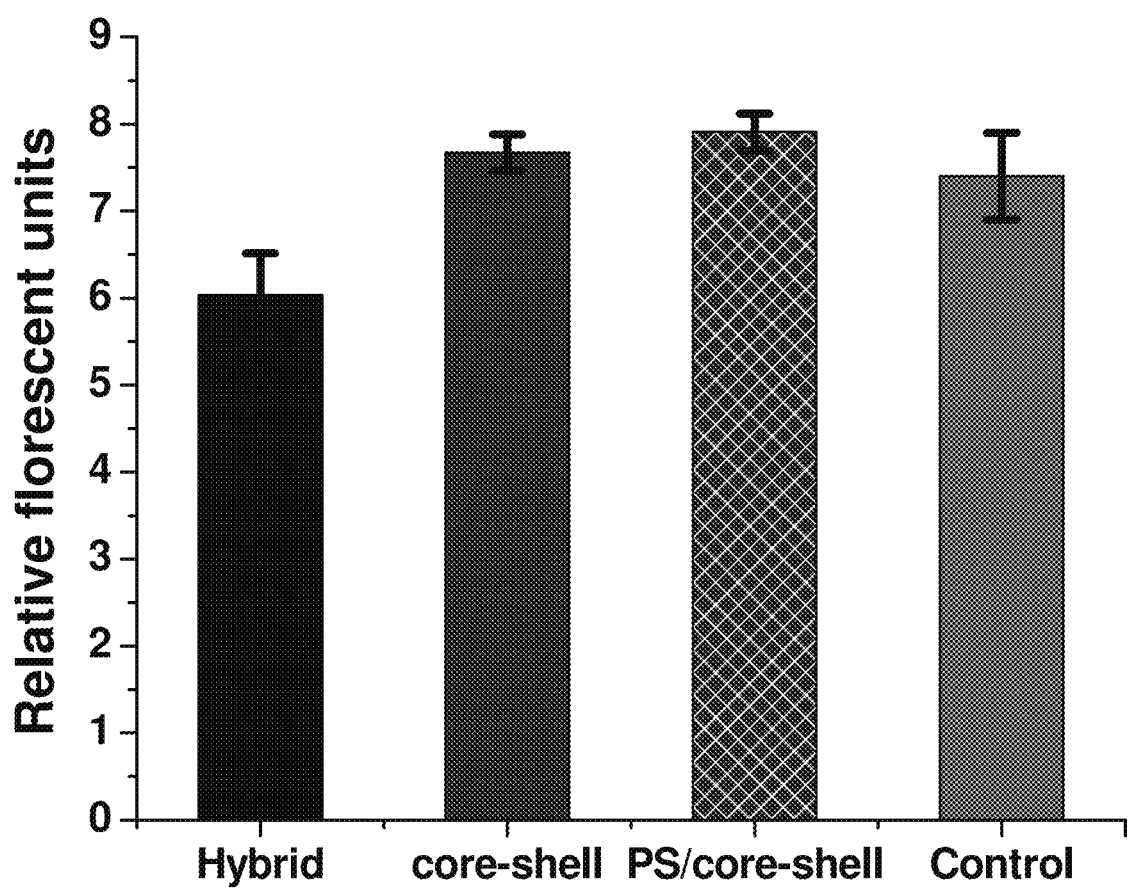
FIG. 9 shows the viability of NIH3T3 fibroblasts as measured by relative fluorescence units after culturing with the scaffold for 24 hours.

MB is also a photodynamic dye, and its concentration-dependent color change at very low concentration ranges can be visualized. Therefore, we used image processing to determine the concentration change of MB after immersing the fibers in PBS media. Visual images of the PBS after immersing the core-shell fiber are given in FIG. 8C, and the relative concentration of MB by image processing is shown in FIG. 8D. A mathematical model was devised (see Methods & Materials section) according to relative intensity change between red, green and blue (RGB) color following calibration with a known concentration of MB (FIG. 9). The results indicate that both hybrid and PCL fibers experience a different level of initial burst release. However, in the case of core-shell fibers, the release of MB was directly proportional to the dissolution rate of the core fiber layer. This suggests PCL shell layer coating prevents burst release and provides a prolonged drug release profile.

Figures 10A, 10B, 10C:
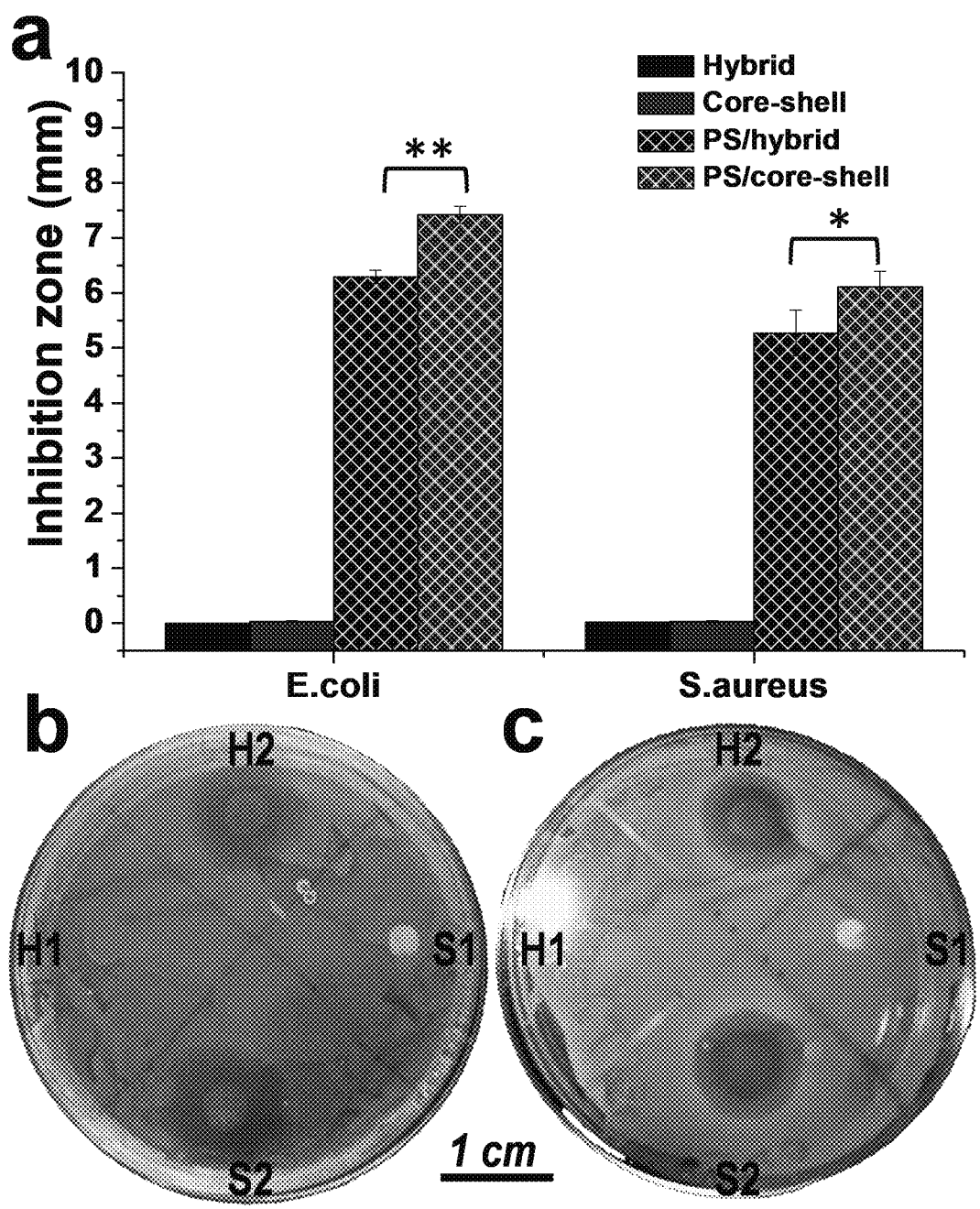
FIGS. 10A-10C show the inhibition zone of the PS-loaded fibrous scaffolds against *E. coli* and *S. aureus*. 10A shows the diameter of the inhibition zone, calculated as an average of three experiments. 10B shows a representative inhibition zone of the scaffolds against *E. coli*. 10C shows a representative inhibition zone of the scaffolds against *S. aureus*. Where H1 and S1 represent hybrid and core-shell fibrous scaffold, H2 and S2 represent PS-loaded hybrid and core-shell fibrous scaffold.

The effect of drug release behavior was tested using the bacterial inhibitory effect of penicillin/streptomycin (PS) loaded into the substrates against the common pathogens namely, *E. coli* and *S. aureus*. Both PS loaded hybrid scaffold and core-shell fibrous scaffolds showed a clear inhibition zone against *S. aureus* and *E. coli* bacterial strains. Core-shell fibrous scaffolds showed a superior inhibition effect, compared to that of hybrid scaffold against both pathogens, shown in FIG. 10A, as measured by the diameter of the inhibition zone, calculated as an average of 3 experiments. This implies the controlled release of antibiotics improves inhibitory potential against bacterial strains by maintaining a constant and localized release of therapeutics. FIG. 10B shows a representative inhibition zone of the scaffolds against *E. coli*. FIG. 10C shows a representative inhibition zone of the scaffolds against *S. aureus*. H1 and S1 represent hybrid and core-shell fibrous scaffold, H2 and S2 represent PS loaded hybrid and core-shell fibrous scaffold. PS loaded core-shell fibrous scaffolds showed better antibacterial performance than that of hybrid scaffolds due to the controlled release of the antibiotics. Both scaffolds showed a smaller inhibition zone against *S. aureus*, compared to *E. coli*. More interestingly, a double zone of inhibition was observed in the case of *S. aureus*, in which the inner zone was darker than the outer one, indicating that tolerance of *S. aureus* to PS was higher than for *E. coli*.

Example 6

Figure 11:
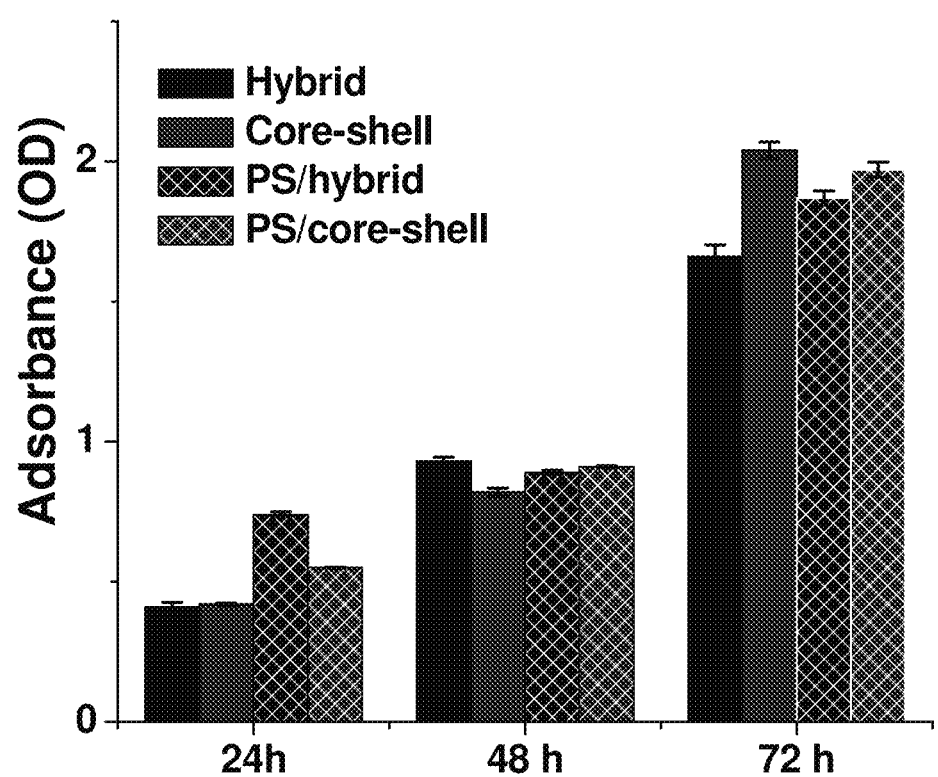
FIG. 11 shows an MTT assay, used for assessing cell proliferation and metabolic activity, following culture of bone marrow mesenchymal stem cells (BM-MSCs) for 24, 48, and 72 h. Individual fibers show an increase in cell proliferation with time. The values are expressed as mean±SD from three independent experiments.

In most in vitro wound healing studies, dermal fibroblast cells are used. However, recent literature suggests that bone marrow-derived mesenchymal stem cells (BM-MSCs) have a number of advantages including higher re-epithelialization rate, better cell infiltration, and angiogenic effects (McFarlin et al. 2006, *Wound Repair & Regen* 14:471-478; Chen et al. 2012, Frontiers in Immuno 3:doi:10.3389/fimmu.2012.00192). However, the BM-MSCs typically have a lower tolerance to reagents in comparison to fibroblasts. Therefore, we tested the cytocompatibility of PS loaded scaffolds using BM-MSCs in vitro. Furthermore, in clinical applications, a patient's own cells could be utilized for developing cell-laden scaffolds and dressing leading to improved chronic non-healing ulcer treatment. As shown in FIG. 11, the adhesion and growth of BM-MSCs were observed with both PS loaded and control scaffolds through 72 hr, and an MTT assay was performed following the culture of bone marrow mesenchymal stem cells (BM-MSCs) for 24, 48 and 72 h. Individual fibers show an increase in cell proliferation with time. The values are expressed as mean±SD from three independent experiments. All the scaffolds showed good biocompatibility, and the incorporation of PS as an antibiotic within PCL coated hybrid scaffolds did not show any significant negative effects on the cell proliferation. There were no significant differences in cell proliferation between the control and loaded scaffolds. The incorporation of PS within PCL coated hybrid scaffolds did not affect cell proliferation on the produced fibrous mats. Similarly, using NIH 3T3 cells we observed minimal negative viability effect. Specifically, the proliferation rate of cultured 3T3 cells in the presence of various electrospun scaffolds was assessed by PrestoBlue™ Cell Viability Reagent at 24 h of culture. The results showed similar metabolic activity and proliferation between scaffolds and control cells during the culture period. As such, these core-shell fibrous scaffolds demonstrate utility as a novel biomaterial-based wound dressings with sustained controlled drug release that improves healing and treatment outcomes.

CONCLUSION

Nanofibrous mats formed from core-shell nanofibers were fabricated using co-axial electrospinning in which the core was a hybrid of CL/PGS surrounded by a PCL shell. SEM result showed that the hybrid fibers preserved their morphological integrity after coating. It was confirmed by TEM and XPS that the PCL shell layer was much thinner than the core layer. Therefore, the presence of PCL encapsulation did not significantly influence the thermal or the mechanical properties of the core fiber. However, a significant retarding effect of PCL coating on the dissolution rate of the hybrid fiber was observed. Ultimately, the PCL coated hybrid fibers had a much longer shelf life and provided sustainable drug release. Antibiotics were successfully loaded into the core-shell fibers, and their release showed superior antibacterial effects against the common bacterial pathogens found on the skin without causing any observable cytotoxicity. Taken together, these core-shell based biomaterials provide novel drug-releasing biomaterials for wound dressing and healing application. Another benefit of the invention is its utilization of biomaterials otherwise considered to be waste products, thus providing additional ecological, societal and economic benefits.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

ACKNOWLEDGEMENTS

This project was funded by the Science and Technology Unit—King Abdulaziz University—Kingdom of Saudi Arabia, award number UE-41-106.

We claim:
1. A method of preparing a controlled-drug release-based wound dressing scaffold by co-axial electrospinning, comprising core-shell nanofibers
   wherein
      an outer shell coating layer of the scaffold comprises polycaprolactone (PCL) formed from a solution of 6-8% PCL by weight/volume in 9:1 chloroform and ethanol, wherein the PCL has a molecular weight of at least 70,000 Da; and
      a core gel layer of the scaffold comprises a mixture of chitin, lignin, polyethylene oxide (PEO) and polyglycerol sebacate (PGS),
      wherein the outer shell coating layer encapsulates the core gel layer,
      wherein the core-shell nanofibers have an average diameter in the range of 100 to 500 nm and the shell has a thickness in the range of 5 to 100 nm,
      wherein the scaffold is produced by electrospinning the PCL solution at a feed rate in the range of 0.4 to 0.7 mL/hr, and a mixture of an aqueous solution of chitin, lignin and PEO and a PGS solution in ethanol at a feed rate in the range of 0.1 to 0.3 mL/hr, and
      wherein the scaffold is configured to provide a controlled rate of release of at least one drug, agent and/or bioactive nanoparticle.

2. The method of claim 1, wherein the core gel layer is formed by mixture of
   aqueous solution of chitin, lignin and PEO, and
   a PGS solution in ethanol.

3. The method of claim 2, wherein the concentration of lignin is in the range of 0.05 to 2.0 wt %, the aqueous dispersion of chitin nanofibrils (2% w/v) is in the range of 25 to 200 wt %, and the PEO is in the range of 7 to 10 wt %.

4. The method of claim 2, wherein the PGS solution in ethanol comprises 10-30% weight/volume of PGS.

5. The method of claim 2, wherein volume ratios of the mixture of
   the aqueous solution of chitin, lignin and PEO, and
   the PGS solution in ethanol
are in the range of 100/0 to 85/15.

6. The method of claim 1, wherein the co-axial electrospinning is performed at 18 kV of voltage, having a needle-to-collector distance in the range of 12 cm to 14 cm.

7. The method of claim 1, wherein the at least one drug, agent and/or bioactive nanoparticle are in the core gel layer.

8. The method of claim 7, wherein the outer shell coating layer is configured to provide the controlled rate of release of at least one drug, agent and/or bioactive nanoparticle from the core gel layer.

9. The method of claim 1, wherein the outer shell coating layer is configured to provide adhesion to skin or a wound surface.

10. The method of claim 1, wherein at least one drug, agent and/or bioactive nanoparticle is an antimicrobial nanoparticle made of a material selected from the group consisting of silver, copper oxide and zinc oxide.

11. The method of claim 1, wherein the at least one drug, agent and/or bioactive nanoparticle is a water/ethanol soluble antibiotic selected from the group consisting of penicillin, streptomycin, amoxicillin, doxycycline, cephalexin, ciprofloxacin, clindamycin, metronidazole, azithromycin, sulfamethoxazole, trimethoprim, clavulanate and levofloxacin, and derivatives thereof to inhibit or treat a microbial infection.

12. The method of claim 1, wherein the at least one drug, agent and/or bioactive nanoparticle is a water soluble antioxidant selected from the group consisting of vitamin C, glutathione and uric acid, and wherein the water soluble antioxidant is in the core gel layer.

13. The method of claim 1, wherein the at least one drug, agent and/or bioactive nanoparticle is an oxygen-releasing agent selected from the group consisting of $CaO_2$, magnesium peroxide ($MgO_2$), hydrogen peroxide ($H_2O_2$), manganese dioxide, zinc oxide, or sodium percarbonate ($(Na_2CO_3)_2$), and wherein the oxygen-releasing agent is in either the outer shell coating layer or in the core gel layer.

14. The method of claim 1, wherein the at least one drug, agent and/or bioactive nanoparticle is a growth factor or a growth factor peptide mimetic selected from the group consisting of angiopoietin, bone morphogenetic proteins, ciliary neurotrophic factor, leukemia inhibitory factor, interleukin family members (such as IL-6), colony-stimulating factors (GM-CSF, M-CSF and G-CSF), epidermal growth factor, ephrin family members, erythropoietin, fibroblast growth factor family members, growth differentiation factor-9, hepatocyte growth factor, hepatoma-derived growth factor, insulin-like growth factors, keratinocyte growth factor, macrophage-stimulating protein, myostatin, neuregulin family members, neurotrophin family members, platelet-derived growth factor, renalase, thrombopoietin, transforming growth factors, tumor necrosis factor-alpha, vascular endothelial growth factor, and Wnt signaling pathway members, wherein said at least one growth factor is able to stimulate tissue growth, and wherein the growth factor is in either the outer shell coating layer or the core gel layer.

15. A method of preparing a controlled-drug release-based wound dressing scaffold by co-axial electrospinning, comprising core-shell nanofibers, wherein
    an outer shell coating layer of the scaffold comprises polycaprolactone (PCL) formed from a solution of 6-8% PCL by weight/volume in 9:1 chloroform and ethanol, wherein the PCL has a molecular weight of at least 70,000 Da, and wherein the outer shell coating layer is configured to provide adhesion to skin or a wound surface;
    a core gel layer of the scaffold comprises a mixture of chitin, lignin, polyethylene oxide (PEO) and polyglycerol sebacate (PGS) and wherein at least one drug, agent and/or bioactive nanoparticle is incorporated into the core gel layer;
    wherein the core-shell nanofibers have an average diameter in the range of 100 to 500 nm;
    wherein the scaffold is produced by electrospinning the PCL solution at a feed rate in the range of 0.4 to 0.7 mL/hr, and a mixture of an aqueous solution of chitin, lignin and PEO and a PGS solution in ethanol at a feed rate in the range of 0.1 to 0.3 mL/hr; and
    wherein the scaffold is configured to provide a controlled rate of release of the at least one drug, agent and/or bioactive nanoparticle through the outer shell coating layer.

16. The method of claim 8, wherein the outer shell coating layer is configured to provide adhesion to the wound by treating the scaffold with polydopamine.

17. The method of claim 15, wherein the outer shell coating layer is configured to provide adhesion to the wound by treating the scaffold with polydopamine.

* * * * *